United States Patent [19]

Müller

[11] Patent Number: 4,768,875
[45] Date of Patent: Sep. 6, 1988

[54] ARRANGEMENT FOR MAKING CONTACTLESS SECTION-LIKE MEASUREMENTS OF THE FORM OF CURVED OPTICALLY EFFECTIVE SURFACES

[75] Inventor: Ortwin Müller, Aalen, Fed. Rep. of Germany

[73] Assignee: Carl-Zeiss-Stiftung, Heidenheim, Fed. Rep. of Germany

[21] Appl. No.: 917,730

[22] Filed: Oct. 10, 1986

[30] Foreign Application Priority Data

Oct. 12, 1985 [DE] Fed. Rep. of Germany ....... 3536513

[51] Int. Cl.$^4$ .............................................. A61B 3/10
[52] U.S. Cl. .................................................... 351/212
[58] Field of Search ....................... 351/212, 214, 247; 350/420; 356/1, 376

[56] References Cited

U.S. PATENT DOCUMENTS 4,019,813  4/1977  Cornsweet et al. ................. 351/212

Primary Examiner—Rodney B. Bovernick
Assistant Examiner—P. M. Dzierzynski
Attorney, Agent, or Firm—Walter Ottesen

[57] ABSTRACT

A light section is generated on the object with an arrangement for the contactless section-like form measurement of curved surfaces by means of an optical detector functioning in a raster-like manner. The light section is received at an angle inclined to the viewing axis by an anamorphotic system and imaged onto a receiver.

3 Claims, 2 Drawing Sheets

ARRANGEMENT FOR MAKING CONTACTLESS SECTION-LIKE MEASUREMENTS OF THE FORM OF CURVED OPTICALLY EFFECTIVE SURFACES

FIELD OF THE INVENTION

The invention relates to an arrangement for making contactless section-like measurements of the form of curved optically effective surfaces by utilizing an optical detector operating in a raster form.

BACKGROUND OF THE INVENTION

Such arrangements are used in optics for the eye for determining the radius of curvature of the cornea. This is so, for example, because a precise knowledge of the corneal curvature is required for fitting a contact lens.

An apparatus for measuring the curvature of the cornea is disclosed, for example, in DE No. 26 41 004 C2. With this known apparatus, light points are generated on a carrier surface arranged in front of the patient's eye with these light points being virtually imaged on the cornea to be measured; also, a position-sensitive detector is provided for determining the position of the virtual light point corresponding to the particular light point. The disadvantage here is that the required imaging quality of the virtual light points is dependent on the local surface characteristic of the cornea to be measured and can be influenced in the measuring system in only a very limited manner.

Another known method for measuring the form of curved optically effective surfaces, such as exemplified by the cornea of the eye, is the so-called light-section method which, for example, can be carried out with slit lamps of known configuration. In this method, a narrow slit-shaped light beam is transmitted meridianly onto the surface to be measured with the section curve conjointly defined by this "light plane" and the surface being visible from the side as a consequence of stray reflections. The method directly provides the location curve of the meridian section.

When measuring the corneal configuration of the living eye and with the patient fixing the eye onto a mark localized in the axis of the illumination, one guides the light section centrally through the pupil of the eye so that the position of the sight axis with respect to the corneal surface is definitively determined. One can also determine the thickness of the cornea with this method because not only is the form of the outer surface of the region to be measured detectable, but also the form of the inner surface.

The disadvantage of this method is that for the interpolation of the entire surface, successive pluralities of meridian curves must be provided and that a satisfactory precision can only be reached if photographic pictures having sufficient imaging standards can be measured with a measuring microscope and a computed correction corresponding to the conditions for making the pictures is undertaken. An automation of the method with raster-electronic imaging detectors is opposed by their limited resolution since the state of the art requires that the entire meridian section be detected in one traversal.

SUMMARY OF THE INVENTION

In view of the foregoing, it is an object of the invention to improve the light-section method together with the application of raster-electronic optical sensors so that a precise and quick measurement of optical surfaces is possible and especially of the cornea of the human eye.

The arrangement of the invention is for making contactless segment-like measurements of the form of a curved optically effective surface and includes an optical detector operating in a raster format.

According to a feature of the arrangement of the invention, an apparatus for generating the light section on the surface to be measured has an axis and is combined with an anamorphotic system for receiving an image of the light section at a predetermined angle with respect to the axis of the apparatus and for imaging the light section on the optical detector. The apparatus includes slit means mounted on the axis and defining a slit and projection lens means mounted on the axis for projecting the slit onto the surface to be measured.

An anamorphotic imaging is known to be a form of imaging by means of optical systems in which the enlargement is different in two directions running at right angles to each other. Such an optical imaging system can be realized, for example, with a system of crossed cylinder lenses.

In a preferred embodiment of the invention, two imaging anamorphotic systems arranged symmetrically to the main apparatus axis are provided with respective deflection elements. Both deflecting elements image an object point lying on the main apparatus axis into a congruent imaging point on this same axis.

As an optical detector for the adjustment of the apparatus, a monitor can be provided which provides an overview image of the eye to be examined.

BRIEF DESCRIPTION OF THE DRAWING

The invention will now be described with reference to the drawing wherein.

DESCRIPTION OF THE PREFERRED EMBODIMENTS OF THE INVENTION

Figure 1:
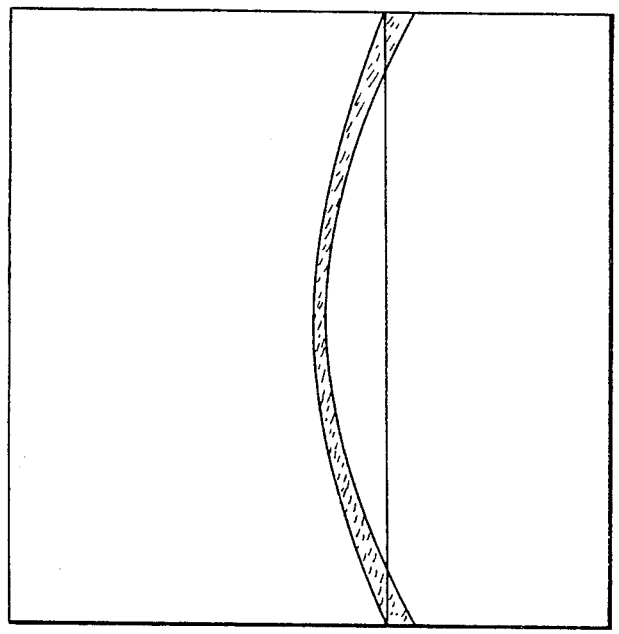
FIG. 1 is a schematic representation of the cornea in the conventional light-section method.

The representation of FIG. 1 shows a conventional light section produced with a slit lamp taken through a human cornea. Assuming that the cornea has a spherical curvature of r=8 mm and a diameter of 10 mm, then a vertex of the meridian curve of 1.2 mm results for a viewing angle of 45° which is therefore 12% of the diameter. This corresponds to 60 pixel with a resolution of 500 pixel in the side. The accuracy required for the application should be 1% thereof or 0.6 pixel. An image on a raster receiver does not provide this precision.

Figure 2:
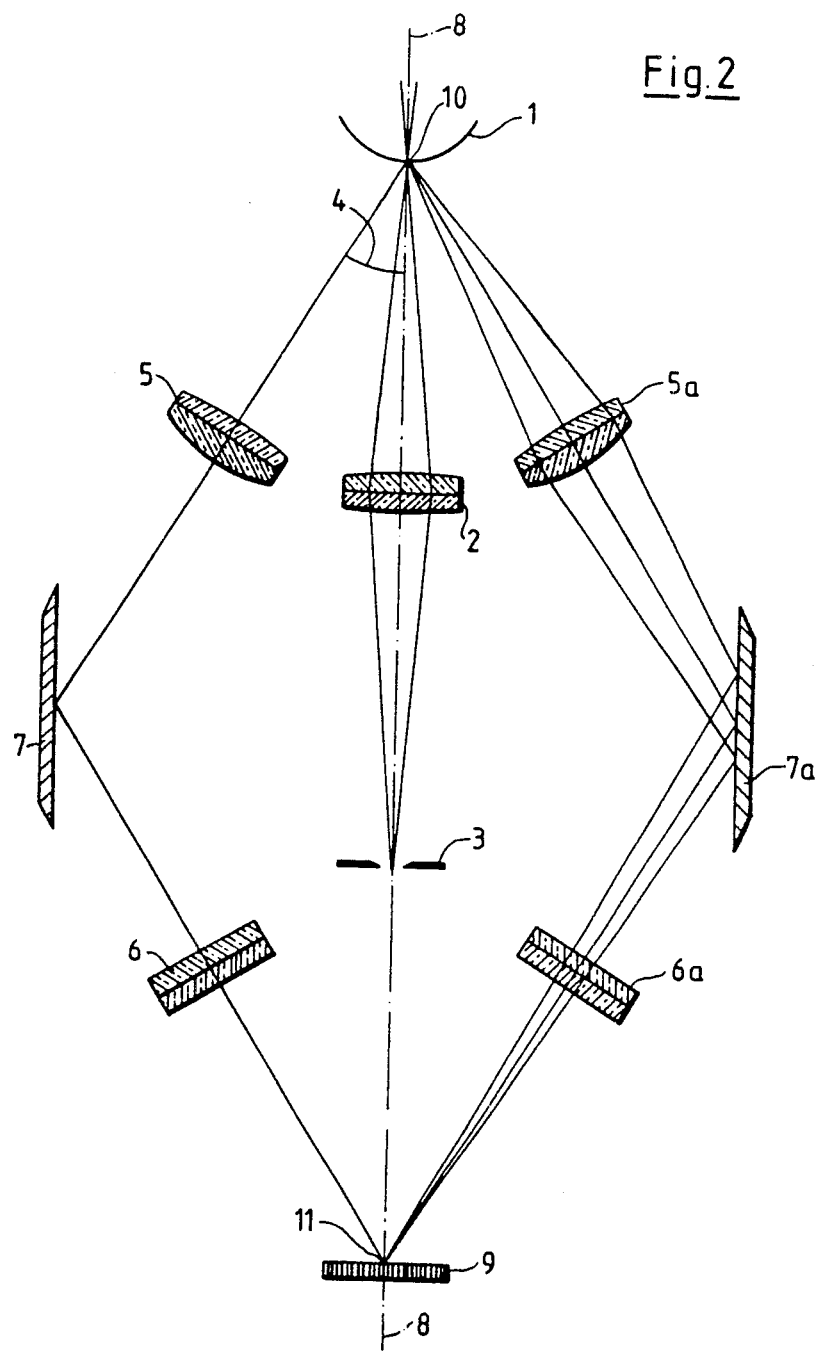
FIG. 2 is a schematic of an embodiment according to the invention with two anamorphotic systems arranged symmetrically to the main apparatus axis; and, FIG. 3 is the image of a spherically curved surface taken with the apparatus according to the invention with the image being shown on a target.

In the schematic representation of the arrangement of FIG. 2, the slit 3 is projected onto the test surface 1 (cornea) by means of projection optical component 2. The rearward imaging optical system mounted at the axis angle 4 is an anamorphotic system which includes the components 5 and 6. Reference numeral 7 identifies a deflecting mirror which assures that the section image again lies unreversed in the main apparatus axis 8 whereat a raster electronic optical receiver 9 is located.

A second anamorphotic system 5a, 6a is mounted symmetrically to the main apparatus axis 8 and has a second deflection mirror 7a. By means of the reflection, it is achieved, that the system is sufficient in approximation to the Scheimpflug condition. This means, that the object plane and the section plane are sharply imaged onto the receiver surface. Since the optical receiving system is provided in duplicate (5, 6 and 5a, 6a), the object and axis point 10 is imaged onto one and the same axis imaging point 11 by means of both optical systems.

Figure 3:
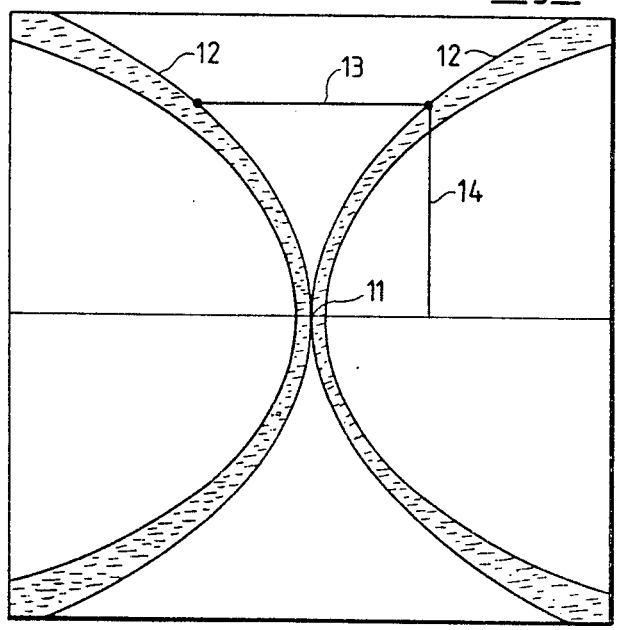

The image shown in FIG. 3 is delivered onto a target from a spherically curved object by means of the arrangement according to the invention. In the image of FIG. 3, the meridian section curves are shown as two elliptical curves 12 which are superposed at the vertex and axis point 11. The measuring distance 13, which corresponds to the latitude circle elevation 14, is so large that the measuring raster can be optimally utilized. With a cathode radiation receiving tube, one can align the measuring direction with the line scanning direction. The measuring elevation is then defined by means of the line number. The reconstruction of the object-meridian curve as well as the interpolation of the entire surface from the discrete sections does require a substantial computing effort which is not difficult and which can be carried out with a conventionally available computer.

It is understood that the foregoing description is that of the preferred embodiments of the invention and that various changes and modifications may be made thereto without departing from the spirit and scope of the invention as defined in the appended claims.

What is claimed is:

1. Arrangement for making contactless section-like measurements of the form of the cornea of the eye, the arrangement comprising:
    an apparatus for generating a plurality of light sections on the surface of the cornea, the apparatus having a main axis and including:
    slit means mounted on said axis and defining a slit;
    projection lens means mounted on said axis for projecting said slit onto said corneal surface; and,
    an imaging anamorphotic system for receiving an image of said light section at a predetermined angle with respect to said axis and for forming anamorphotic images of said light sections wherein the enlargement of said images is different in two directions running at right angles to each other;
    said system including a deflection element and cylinder lens means coacting therewith for imaging a point of said surface lying on said axis into an image point also on said axis; and,
    an optical detector arranged on said axis and receiving said anamorphotic images thereon for computing the total corneal surface from said light sections.

2. The arrangement of claim 1, comprising two of said anamorphotic systems arranged symmetrically about said axis, said systems having respective deflection elements and respective cylinder lens means and being adapted for imaging a point of said surfaced lying on said axis into a congruent image point also on said axis.

3. The arrangement of claim 2, said optical detector being a monitor which provides an overview image of the eye to be examined for adjusting said apparatus.

* * * * *